United States Patent [19]

Nuwayser

[11] 4,215,698
[45] Aug. 5, 1980

[54] DENTAL-CARIES DETECTOR

[75] Inventor: Elie S. Nuwayser, Wellesley, Mass.

[73] Assignee: Abcor, Inc., Wilmington, Mass.

[21] Appl. No.: 913,545

[22] Filed: Jun. 8, 1978

[51] Int. Cl.$^2$ ............................................. A61B 5/05
[52] U.S. Cl. .................................... 128/734; 128/776; 128/787; 128/803; 433/32
[58] Field of Search ............. 128/2.1 R, 2.1 Z, 2.1 E, 128/2.1 C, 2 S, 275.1, 303.13, 303.18, 405, 409, 417, 734, 741, 776, 787, 803; 32/40 R

[56] References Cited

U.S. PATENT DOCUMENTS

| | | | |
|---|---|---|---|
| 2,603,753 | 7/1952 | Axelsson et al. | 128/2.1 R X |
| 2,949,107 | 8/1960 | Ziegler | 128/409 X |
| 3,035,580 | 5/1962 | Guiorguiev | 128/303.18 |
| 3,078,850 | 2/1963 | Schein et al. | 128/2.1 E X |
| 3,128,759 | 4/1964 | Bellis | 128/2.1 R |
| 3,753,434 | 8/1973 | Pike et al. | 128/2.1 Z |
| 3,830,220 | 8/1974 | Johnson | 128/417 X |
| 3,901,216 | 8/1975 | Felger | 128/2.1 Z |
| 3,916,529 | 11/1975 | Mousseau | 128/2 S X |
| 4,048,723 | 9/1977 | Thorup | 32/40 R |

FOREIGN PATENT DOCUMENTS 376028 10/1939 Italy ........................................ 128/409

OTHER PUBLICATIONS

Mumford et al., "Electronic Tooth Stimulator . . . ", Biomed Eng., vol. 11, No. 1, pp. 22–23, Jan. 1976.

Primary Examiner—Lee S. Cohen
Attorney, Agent, or Firm—Richard P. Crowley

[57] ABSTRACT

A dental-caries detector for the determination of dental caries by measurement of the electrical conductivity or other electrical property of a tooth, which dental-caries detector comprises: an electrically conductive, caries-detector probe having a probe tip which is adapted to be placed on a wet, electrically conductive area of the tooth; a dry air mechanism for providing a surrounding curtain of drying air about the probe tip to provide a dry, electrically nonconductive area about the probe tip; and a shield surrounding the probe tip to seal the probe tip from the dry area.

22 Claims, 8 Drawing Figures

DENTAL-CARIES DETECTOR

BACKGROUND OF THE INVENTION

It is well known that the electrical properties of teeth change when disease or decay alters the physical composition or structure of the affected teeth. In the past, it has been found that measurement of the change in electrical properties; for example, the resistivity or conductivity of the tooth, provides a rapid, simple and effective means of detecting disease or decay without the difficulties associated with present mechanical probing techniques.

The method of diagnosing caries by measuring electrical resistance was first proposed by Pincus (1951), using DC currents of up to 300 microamps. Mayuzumi, Suzuki and Sunada (1964) extensively studied the electrical resistance and the degree of dental caries and caries susceptibility, and concluded that teeth, having a low electrical resistance, had a high susceptibility to dental caries. The potential applied to the tooth was less than 1 volt AC, and teeth showing electrical resistance of over 600 K had no caries and had low caries susceptibility, whereas teeth with resistance of under 250 K had actual dentinal caries, or most of such teeth suffered caries sooner or later, regardless of sound appearance of pits and fissures of those teeth. Thus, by the measurement of conductivity, it is possible to detect in a meaningful manner whether or not teeth are caries-free or alternatively to detect the existence of early incipient caries, late incipient caries and carious lesions of teeth (see, for example, Japanese Patent No. 280,012).

However, despite the knowledge concerning the detection of caries employing an electrical caries detector, a simple portable instrument has not been developed for the reliable measurement of dental caries employing measurable change in electrical properties of the tooth, such as by the measurement of the electrical resistance or conductivity of the tooth from a prope tip through the dental pulp to a ground.

One difficulty associated with past proposed dental-caries detectors has been the wide variation in electrical-property measurements obtained by the instruments. It has been found that conductivity measurements made on a wet tooth are often not very stable, and such measurements have been suspected of giving false positive values. The presence of a condutive liquid in a deep carious lesion is required during a measurement by a dental-caries detector, to insure good electrical conduct between the probe tip by which the current is applied to the tooth, and which is placed or fixed on the tooth surface and the lesion located well below the tip and within the tooth. There exists a need for a simple, portable, electrical, dental-caries detector which will provide statistically meaningful, reliable and consistent electrical-property measurements and which will overcome the varying and false measurements associated with past detectors.

SUMMARY OF THE INVENTION

My invention relates to an improved dental-caries detector and probe and to a method of construction and use of said dental-caries detector and probe. More particularly my invention concerns a dental-caries detector which includes a detector probe, a shield means surrounding the probe tip of the detector, the shield means adapted to seal a wet, electrically conductive, measurement site to which the probe tip is applied and to shield the probe tip from a surrounding nonconductive dry area, and a drying means to provide a dry, electrically nonconductive area about the sealed, wet, measurement site.

My dental-caries detector is directed to an instrument which will detect dental-caries lesions by measuring the electrical properties of a tooth, particularly the conductivity or resistivity of a tooth. The detector is designed to maintain a wet area or environment at the measurement site of the detector-probe tip and a dry area or environment around such wet measurement site. My dental-caries detector so designed and constructed provides for accurate and reliable electrical measurement. My detector prevents false positive measurement values, due to any potential short circuit between the probe tip and the adjacent tissues which might occur when the wet, conductive, measurement area is not fully electrically isolated.

My detector provides for a drying means, such as an air stream, for drying the tooth surface about the probe tip and also includes a shield means secured to the probe tip to surround completely the tip and to isolate the wet, conductive, measurement area to which the probe tip is applied from the surrounding dry, nonconductive area obtained by the drying air stream.

In another embodiment of my detector, a means is provided for applying or maintaining a conductive liquid to the measurement site through the application of a conductive liquid to the probe tip at the measurement site.

In a further embodiment, I have discovered a detector wherein a shield means may be employed which permits the rapid and easy measurement of the electrical properties of other sites on a tooth which has been previously dryed by the drying air stream, so that the shield means will provide a conductive liquid about the probe tip and measurement site each time that the probe tip and shield means are moved from one site to another site on the tooth or teeth surface.

I have discovered an improved dental-caries detector for the determination of a tooth condition, such as dental caries or other dental conditions, by measurement of the electrical properties of the tooth, particularly the electrical conductivity of the tooth. My detector comprises: a housing, such as an elongated, nonconductive, plastic housing, for example, adpated to be hand-held by the dentist in use; an electrically conductive probe positioned within the housing and having a probe tip extending from the one end of the housing, the tip adapted to be applied during use to a suspected area of the tooth to measure the conductivity of the tooth. My detector includes means electrically connected to the probe tip for applying a designated current, typically a current below the threshold pain level of the patient, such as less than about 1 microamp, to the probe tip, and a fluid passageway preferably within the housing and coaxial about the probe to provide for a surrounding curtain of a drying fluid, particularly air, at the probe tip. In use my detector provides a dry, nonconductive area about the probe tip and the wet, conductive, measurement site to which the probe tip is applied. The detector includes means to supply a drying fluid to the passageway, such as a source of dry air, and appropriate valving means is used to permit the application of the air to the site during measurement. The detector includes a shield means surrounding the probe tip and adapted, when the probe tip is applied to a wet measurement area, to seal the probe tip within the shield and from the surrounding nonconductive dry area, thereby permitting the probe tip to measure accurately and effectively, without false readings, the electrical condition of the tooth.

My invention will be described and illustrated in connection with certain preferred embodiments, although it is recognized and is within the spirit and scope of my invention that various changes, modifications and alterations may be made to my dental-caries detector as described, without departing from the spirit and scope of my invention.

DESCRIPTION OF THE EMBODIMENTS

Figure 1:
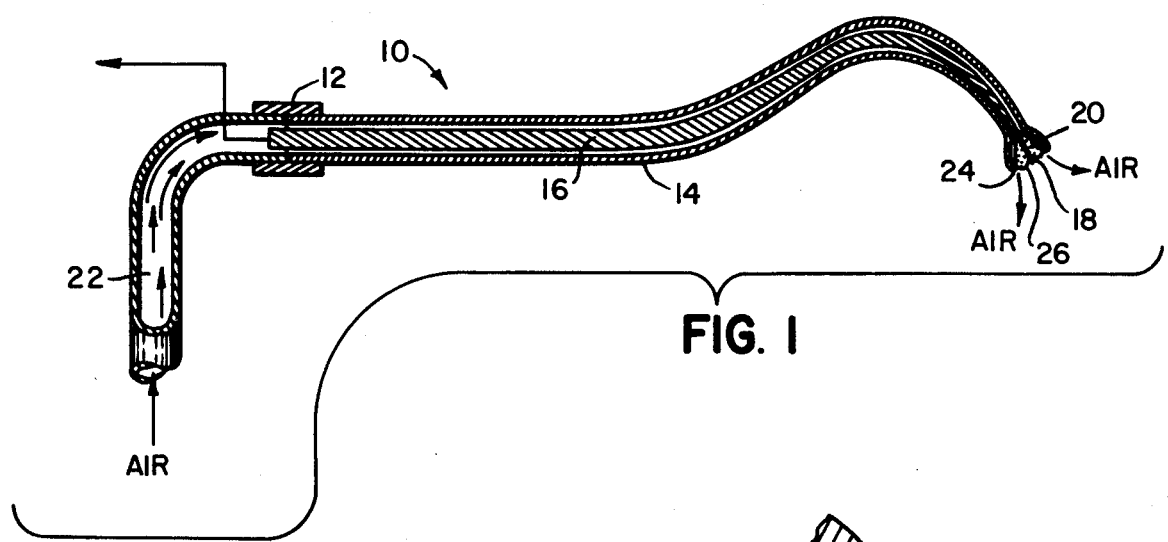
FIG. 1 is an illustrative schematic cross-sectional view of my improved dental-caries detector, showing the probe with a shield at one end thereof.

FIG. 1 shows a dental-caries detector 10 which includes a handle element 12 and an elongated plastic housing element 14 which includes within the housing element 14 an elongated, electrically conductive probe 16 having a probe tip 18 at the one end thereof. A coaxial air passage 22 surrounds the probe 16 throughout the length of the housing element 14, and is adapted to permit air into an inlet through the handle into air passage 22 and to discharge air circumferentially through outlet 24. The probe tip 18 is surrounded by a shield element 20 which in this embodiment includes a concentric inner cavity 26 surrounding the probe tip 18. The shield element 20 is composed of a soft flexible material and is adapted to effect a seal to surround the surface of the tooth on which the probe is placed, so that the area to which the probe tip 18 is applied is effectively isolated from the peripherally surrounding area of the shield 20.

The dental-caries detector 10 permits conductivity measurement made on a wet tooth to be stable and not to give false positive values because of a potential short circuit between the probe tip 18 and the adjacent tissues or the surface of the tooth. In use the shield 20 and its peripheral-sealing lower surface completely surround the probe tip 18, except for the tip 18 which makes electrical contact with the tooth surface in a wet measurement or test area. The shield functions to seal the measurement site of the probe tip and to maintain a wet test area from the drying effect of the air which is passed through the passageway 22 and through the outlet 24.

The improved dental detector permits stable and reproducible conductivity measurement to be made by providing for the surface of the tooth at the point of the probe to be wet and by ensuring that a closed circuit is formed between the probe and the carious lesion below the surface of the tooth. In addition and importantly, the detector also provides for the surface of the tooth in the surrounding area to be kept dry to eliminate short circuits which may occur between the probe tip and adjacent tissues.

In such operation, the presence of fluid in the deep carious lesion of the tooth is required during measurement, to ensure good electrical contact between the probe tip 18, which is applied to the tooth surface, and the carious lesion located within the tooth. The dental-caries detector is designed to maintain simultaneously a wet, measurement, test-site environment at the probe tip and a dry nonconductive area or field about the tip. In use the probe tip 18 is placed on the tooth surface, with gentle pressure exerted toward the tooth surface, to form an effective seal between the shield element 20 and the tooth surface, and, thereafter or simultaneously, drying air from outlet 24 is emitted to dry the area surrounding the shield 20. If desired, additional moisture or other conductive fluid may be employed, either as a liquid or as a hydrogel within the cavity space 26, to ensure the maintenance of a wet conductive measurement or test site when the probe tip touches the tooth surface.

In FIG. 1, a coaxial air passageway 22 for the introduction of dry air is illustrated to dry the surface about the probe tip 18. However, it is recognized and is a part of my invention that any other fluid may be employed, such as other gases, to ensure a dry or nonconductive area about the probe tip 18. In addition, a shield element 20 has been shown in one simple form, and, for example, may be formed of a soft or flexible elastomeric, polymeric or rubber-type material or other solid or cellular material which fits snugly around the probe tip. However, it is recognized and is a part of my invention that the shield means may be made from a wide variety or materials and of different forms and shapes, provided that the shield isolates the wet, conductivity, measurement area surrounding the probe tip to prevent short circuits during the measurement.

A portion of the probe, including the tip, or the probe tip, itself, may be made independently and may be disposable and adapted to fit into the remaining part of the probe. Particularly to reduce infection, the shield means may be disposable and stored in a wet or dry state, ready for attachment to the probe tip, or the shield means may be formed integrally also with a disposable probe tip. Where the shield means is stored in a dry condition, it should be wet with water or other conductive, medically acceptable liquid immediately before placement on the tooth surface, to ensure a wet, good, conductive site for the probe tip, or the internal cavity 26 of the shield means 20 may be filled with a liquid or a hydrogel; that is, a water-bearing polymer, to ensure the conductivity of the measurement site.

Figure 2A:
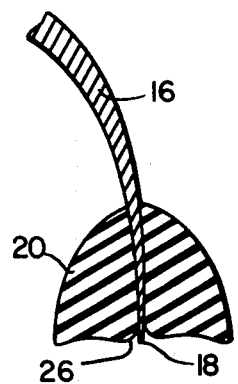
FIGS. 2a through 2d are illustrative schematic cross-sectional fragmentary and enlarged views of the probe of FIG. 1, showing various forms of the shield at the end of the probe.

FIGS. 2a through 2d show various forms and materials from which the shield about the tip may be composed. FIG. 2a illustrates a bell-type shield, as the type as demonstrated in FIG. 1, which is composed of a soft flexible rubber material having a cavity 26 designed to maintain a liquid or gel within the lower surface, and is flexible and adapted to fit snugly against the tooth surface to form a sealing ring about the probe tip 18. The shield is formed to slip over the one end of the probe tip and to be removable if desired.

Figure 2B:
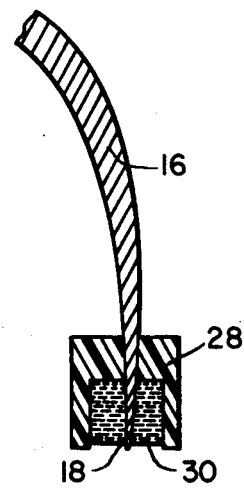

FIG. 2b illustrates another shield composed of a flexible or rubbery material 28 having an internal cavity 30 which includes a porous, wettable foam material; for example, an open-cell urethane foam or other foam-like material, which contains a moisture or salt-conductive mixture or a water gel, such as a water-bearing polymer, such as a hydrogel. In operation, the peripheral edges of the soft material 28 form an effective seal about the probe tip 18, while the hydrogel or porous, wettable material in the cavity 30 insures a good, wet, conductive test site for the probe tip.

Figure 2C:
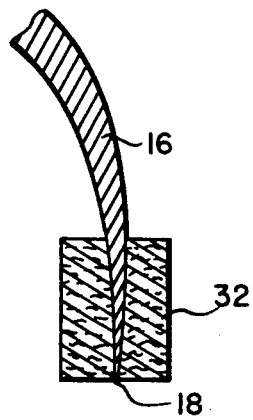
Figure 2D:
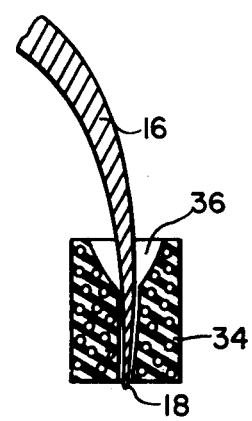

The embodiments as illustrated in FIGS. 2b, 2c and 2d are identified as wet-shield means, rather than dry-shield means, which only serve to seal the measurement site. The wet shield is particularly advantageous in that it permits additional measurement of the conductivity of other test sites on the tooth which had been previously dried by the drying air stream from the detector. Therefore, the detector with such wet-shield means may be moved around on the tooth surface, and, by gentle pressure on the shield, the wet shield releases a fluid to the surface of the tooth about the probe tip to ensure a wet, conductive, measurement site. The wet-shield means permits the simultaneous formation of a wet measurement site, as well as sealing the wet measurement site from the dry surrounding nonconductive field.

FIG. 2c illustrates a shield means which comprises a totally wet shield composed of a conductive, liquid-containing material 32 about the probe 16 and the probe tip 18 of, for example, an open-cell foam, such as a urethane foam, felt or other retaining means containing water or other conductive liquid, which is released to the tooth surface on the application of gentle pressure. The porous or wet shield 32 is a material which will retain moisture to ensure a wet conductivity site, and must also serve to seal the probe tip from the wet site.

FIG. 2d shows a shield element 34; for example, of rubber, adpated to seal the site, with a reservoir 36 which contains water or a conductive liquid which is adapted to flow from the reservoir 36 about the probe tip at the measurement site.

Figures 3, 4:
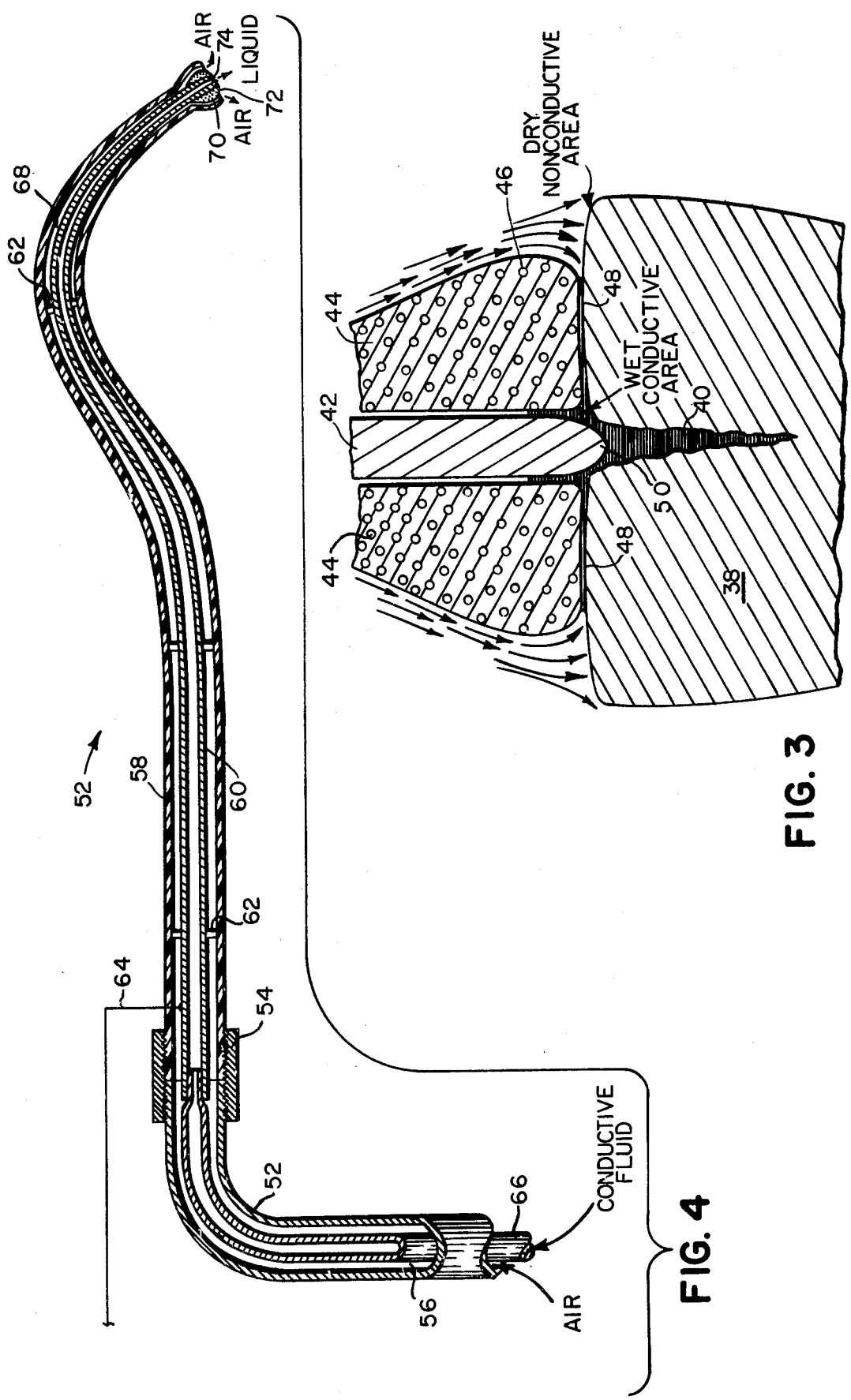
FIG. 3 is a greatly enlarged schematic illustrative cross-sectional view of the probe tip and shield in use in determining the conductivity of a tooth having a dental-caries lesion.
FIG. 4 is an illustrative schematic cross-sectional view of another embodiment of my dental-caries detector employing a means to apply a conductive liquid to the measurement site.

FIG. 3 illustrates one embodiment showing a tooth 38 having a carious lesion 40 filled with a fluid and a probe 42 having a probe tip 50, with a wet-shield element 44 having within open foam cells a conductive liquid 46, such as water, with the lower part of the shield 44 forming an effective seal between the foam and the tooth surface 48. The porous, fluid-filled shield 44 surrounding the probe 42 forms a wet, conductive, measurement site for the probe tip 50, so that the lesion is filled with a fluid, thereby permitting good electrical contact between the probe tip 50 and the bottom of the lesion 40, to produce a reproducible and stale conductivity measurement.

In contrast, a dry carious lesion on the same tooth; that is, without the presence of a liquid, on the contacting of the probe tip 50, would not permit electrical contact between the probe and the bottom of the lesion, without the presence of a wet conductive liquid, either naturally on the tooth or within the porous structure of the tooth, or preferably aided by the gentle pressure on the wet-shield element 44 to discharge the liquid 46 from the foam 44 to and about the probe tip 50 to form a wet measurement site.

FIG. 4 illustrates another embodiment of a dental-caries detector 52 which includes an air-hose connection 54 and an air hose 56 to introduce air coaxially about a housing 58. The detector 52 comprises a fluid-filled metallic or metal-coated tube 60 positioned by spacers 62 within the housing 58, with one end of the tube 60 tapering to a point as a fluid-delivery probe tip 74 of the type, for example, used in delivering ink in ballpoint pens or felt-tip pens. The probe tip 74 is surrounded by a shield 72 to prevent drying by the surrounding air issuing from outlet 70 from the coaxial air passage. The tube 60 is filled with any fluid which is conductive, cariostatic, bacteriostatic or contains fluoride or any other drug or antibody which reduces infection, improves lesion detection or improves conductivity or dental health.

An electrical connection 64 contacts the tube 60, with the connection made at any point along the tube, so long as the electrical connection is made with the fluid of the tip of the tip 74. The tube 60 may be composed of a plastic with only a part made metallic, with the electrical connection 64 connected to the metallic portion. It also is preferable to employ a clear or transparent plastic tube 60 to assist the dentist in determining the amount of fluid still retained within the tube, provided, of course, that the surrounding air duct and housing 58 are also clear plastic, so that the extent of the fill of the fluid in tube 60 may be determined easily.

Surrounding the tube 60 is a coaxial air duct 68 connected to the air hose 56 to deliver air coaxially about the probe tip 74 directly onto the surrounding tooth surface. The duct 68 may be made from a nonconductive polymer material, clear or opaque, or from conductive metal which, in the latter case, should be insulated from the metallic inner tube 60 with appropriate insulating materials or spaces 62 as illustrated, which do not hinder the passage of air in the coaxial duct 68. Similar to the detector of FIG. 1, the detector probe may be entirely disposable or portions thereof disposable. Typically the fluid employed within the tube may be a conductive fluid, such as aqueous saline solutions, so that, on admission of air into the one end of the fluid, the fluid is delivered via the electrical conductivity probe tip into the measurement area, to provide for a conductive material about the wet measurement site, or where conductive material is not required, then other material as set forth may be delivered to the measurement site during measurement.

As described, it is important that the measurement site be wet or conductive, and, accordingly, the natural water on the tooth surface, such as the saliva, or water within the internal tooth may be employed, or preferably a nontoxic and physiologically acceptable liquid may be applied before the measurement or shield means, dry or wet, is dipped into a conductive solution, or the conductive solution is delivered directly through the tube. A wide variety of conductive materials can be employed, including various salt solutions, sodium-chloride solutions and agar gel or EKG gel commonly employed for conductive measurement, particularly of metallic conductors, such as suspensions of fine, metallic, particulate materials, such as silver, carbon particles and the like. The conductive material may be a solution, suspension paste or solid material, and may contain conductive salts, water or other additives, such as suspending agents, detergents, emulsifiers, bacteriostats, thickeners, polymers, gels, stabilizers, antibiotics and the like.

In the operation of the detector of FIG. 4, the probe tip 74 is placed on the measurement site, the drying air is discharged from outlet 70 to dry the area surrounding the shield 72 which seals the probe tip 74, and air is admitted into one end of the tube 60 to force from the probe a liquid to the measurement site.

Figure 5:
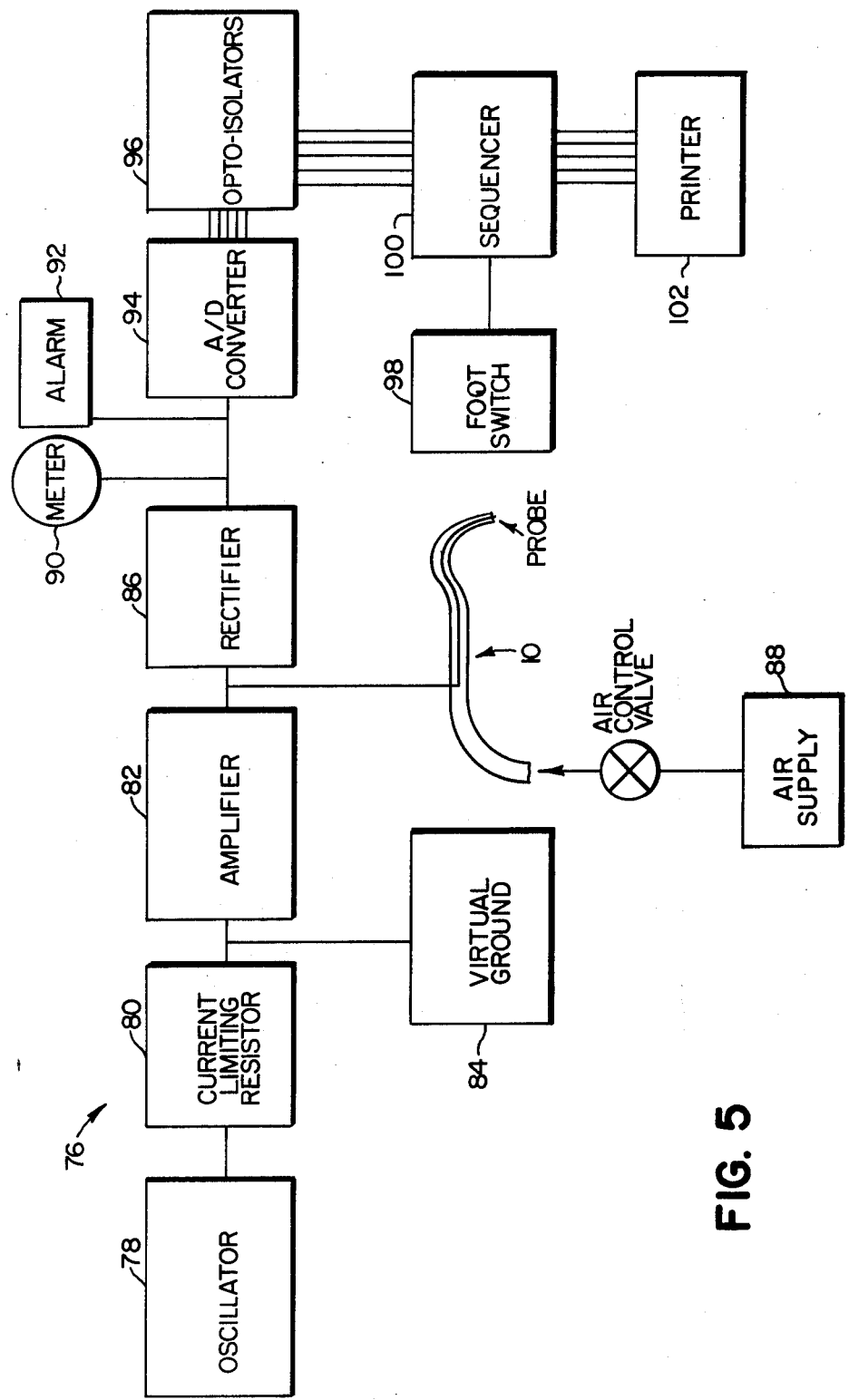
FIG. 5 is a block-flow diagram of a dental-caries-detector system employing my dental-caries detector.

A block diagram of a detector system, in which my detector probe may be employed, is illustrated in FIG. 5. The detector system is powered by batteries (plus 3 volts, minus 3 volts not shown), which batteries supply power for the oscillator and all other low-power components to the left of the optoisolators. The sequence and printing means typically require higher power; for example, plus 18 to minus 18 volts of a rechargeable battery power (not shown). The detector system comprises an oscillator 78 which generates an electrical sinusoidal wave of low frequency (for example, 20 Hz) through the current-limiting resistor 80, which resistor provides that no more than one microamp of current passes through the patient or to the probe tip. The operational amplifier 82 controls the voltage at the amplifier output, which voltage output is proportional to the input current and is proportional to the resistance of the patient's tooth being tested. The amplifier 82 receives current from the current-limiting resistor 80 and keeps the input current at a virtual ground point by passing current through the patient. Most of the resistance of the patient to the passage of the current occurs in the enamel layer of the tooth which is being tested with the detector 10. The voltage output of the operational amplifier 82 is proportional to the resistance of the patient, including the enamel of the tooth being measured, wherein most of the resistance arises. The other patient resistance is in the probe 10 and the ground 84 which may be, for example, a hand-held virtual ground held by the patient or by the dentist, or a desired ground can be secured by electrical contacts secured to the patient's skin or lips.

The measured tooth resistance is then displayed and/or recorded for use and evaluation by the dentist. The proportional output signal from the amplifier is directed to rectifier 86 to provide a rectified Dc-analog signal, which signal is then optionally displayed on a meter 90. The resistance or conductivity of the tooth being tested is placed on display by the meter to the dentist for evaluation. When the resistance is less than the preset value of an alarm 92, the dentist is alerted, either through audio or visual means or a combination thereof, that the particular tooth being tested and the measuring-site area is or may be carious, due to its lower resistance in comparison to the preset resistant level of the alarm or meter. The DC-analog signal is then converted to a digital signal employing an analog-digital converter 94. The digital signal in light form is then passed to optoisolators 96, such that only light beams can pass between high- and low-voltage portions of the circuit. The foot switch 98 is employed by the dentist to activate a sequencer 100 which sequences, on demand by the dentist, and activates the printer, so that the signal from the measurement site and displayed on the meter 90 may be printed.

On activation of the foot switch 98, the sequencer sequences the most significant digit to the least significant digit, with the decimal point inserted at the appropriate time. The sequencer is connected to a commercially available printer 102 where the measurement information is recorded in print form. Typically the printer is calibrated to read 100 when the leads of a 22-megohm resistor are connected in place of the patient ground 84 and the probe 10. The printer is selected such that the resistance/printout relationship is linear; for example, so that 2.2 megohms yield a digital printout of 10.

A dry, air-supply source means 88 is also shown with a control valve in the total system as described. Of course, if desired, other detector-electrical-instrument circuits and systems may be employed other than that set forth in FIG. 5. The improved detector has been described with particular reference to a single-probe detector. However, it is recognized that my improvements are also equally applicable to multiple-probe detectors where it is desired to obtain and isolate a conductive measurement site.

What I claim is:

1. A dental-caries detector for the determination of tooth condition in a tooth by measurement of electrical properties of the tooth, which dental-caries detector comprises:
   (a) an electrically conductive probe having a probe tip, the probe tip adapted to be placed on a wet, electrically conductive, measurement site on a tooth surface;
   (b) a drying means to provide for a surrounding curtain of dry fluid to be applied about the probe tip and to provide in use a dry, electrically, nonconductive area on the surface of the tooth about the wet test-measurement site to which the probe tip is applied; and
   (c) shield means surrounding the probe tip and adapted in use, when the probe tip is applied to the wet measurement site, to seal peripherally the probe tip by the contact of the shield means against the tooth surface and from the nonconductive dry area about the measurement site, thereby permitting the probe tip to measure in a stable reproducible manner the electrical condition of the tooth.

2. The detector of claim 1 wherein the shield means comprises a soft, resilient, polymeric material, the lower surface of which material is adapted to contact and form with gentle pressure a peripheral seal with the tooth surface and about the probe tip.

3. The detector of claim 1 wherein the shield means comprises a soft, resilient, polymeric material which includes an internal peripheral cavity surrounding the probe tip, which internal cavity is adapted to contain a conductive liquid, thereby ensuring a wet measurement site for the probe tip.

4. The detector of claim 3 wherein the internal cavity contains a conductive liquid to be applied to the measurement site.

5. The detector of claim 1 wherein the shield means comprises a liquid-retaining, porous material which contains a wet conductive material therein adapted to be extruded therefrom upon the application of gentle pressure of the porous material against the tooth surface, thereby forming simultaneously a peripheral seal about the probe tip and providing a wet, conductive, measurement site containing the liquid for the probe tip.

6. The detector of claim 1 wherein the shield means includes a reservoir adapted for fluid communication with the measurement site about the probe tip, and which reservoir contains a conductive liquid therein to maintain the measurement site as a wet, conductive, measurement site when the detector is in use.

7. The detector of claim 1 wherein the shield means comprises an open-cell, conductive, liquid-retaining-foam-shield means, which foam-shield means, under gentle pressure, emits and produces the formation of a wet measurement site and simultaneously seals the wet measurement site from the surrounding tooth surface outside the measurement site.

8. The detector of claim 1 which includes a tube filled with a conductive material, one end of the tube forming the probe tip and adapted to discharge the conductive material within the tube onto the measurement site and means to apply the conductive material within the tube to the probe tip and to the measurement site.

9. The detector of claim 1 which includes means to determine the electrical conductivity of the tooth when the probe tip is applied to the wet measurement site.

10. The detector of claim 9 wherein the means to determine the electrical conductivity includes:
 (a) power means for supplying current and an oscillator means to oscillate the current from the power means, so as to generate a sinusoidal wave of low frequency to the probe tip;
 (b) a current-limiting means to limit the current applied by the oscillator means to the probe tip to not more than one microamp of current;
 (c) current-grounding means to complete the circuit; and
 (d) means to measure the impedance of the passage of current as a measure of the electrical conductivity of the tooth.

11. The detector of claim 1 which includes:
 (a) a housing element;
 (b) a handle externally surrounding one end of the housing element;
 (c) the probe coaxially positioned within the housing element, the probe tip extending slightly from the other end of the housing element; and
 (d) the drying means comprising an air-delivery means comprising an air passageway in the housing element and extending about the probe, the air passageway having an inlet at the handle for the admission of dry air and an outlet surrounding the probe tip for the discharge of drying air to the measurement site.

12. A dental-caries detector for the determination of tooth condition in a tooth by measurement of electrical properties of the tooth, which dental-caries detector comprises:
 (a) a housing;
 (b) an electrically conductive probe within the housing and having a probe tip extending from one end thereof, the probe tip adapted to be placed on a wet, electrically conductive, measurement site on a tooth surface;
 (c) power means electrically communicating with the probe through the housing for applying a designated current to the probe tip for measurement of the conductivity of the tooth;
 (d) a drying means to provide for a surrounding curtain of dry air to be applied about the probe tip and to provide in use a dry, electrically nonconductive area on the surface of the tooth about the wet, test-measurement site to which the probe tip is applied, which drying means comprises
  (i) an air-delivery means comprising an air passageway in the housing and extending about the probe, the air passageway having an inlet at the other end of the housing for admission of dry air and an outlet surrounding the probe tip at the one end of the housing for discharge of dry air to the measurement site, and
  (ii) air-supply means in fluid communication with the air-delivery means to supply dry air to the air-delivery means and to provide said dry area; and
 (e) a shield means surrounding the probe tip and adapted in use, when the probe tip is applied to the wet measurement site, to seal the probe tip peripherally from the nonconductive dry area about the measurement site by the contact of the shield means against the tooth surface, thereby permitting the probe tip to measure in a stable, reproducible manner the electrical condition of the tooth.

13. The detector of claim 1 wherein the shield means includes a reservoir adapted for fluid communication with the measurement site about the probe tip, and which reservoir contains a conductive liquid therein to maintain the measurement site as a wet, conductive, measurement site when the detector is in use.

14. In a method for determining tooth condition by measurement of the electrical properties of a tooth, which method comprises applying an electrical current to a tooth by the contact with the tooth surface of a probe tip to a wet, conductive, measurement site on the tooth surface and measuring the electrical properties of the tooth, the improvement which comprises:
 (a) peripherally sealing by use of a shield material the wet, conductive, measurement site on the tooth surface;
 (b) applying a drying fluid about the peripherally sealed site to form a peripheral, dry, nonconductive area about the sealed site; and
 (c) measuring the electrical properties of the sealed site on the tooth surface.

15. The method of claim 14 which includes employing the shield material to seal the measurement site by the application of gentle pressure against the tooth surface of the shield material about the probe tip.

16. The method of claim 15 which includes applying an electrically conductive liquid retained within the shield material to the measurement site, thereby providing for a wet, electrically conductive, measurement site.

17. The method of claim 14 which includes applying a wet, electrically conductive liquid to the measurement site through the probe tip.

18. The method of claim 14 which includes employing the shield material to apply a wet conductive liquid to the measurement site by forcing the liquid from a porous, liquid-containing shield material.

19. The method of claim 18 wherein the shield material comprises a resilient, porous foam material secured to and about the probe tip.

20. The method of claim 14 wherein the sealing and the applying of a drying fluid occur substantially simultaneously with the application of the probe tip to the measurement site.

21. The method of claim 14 wherein applying a drying fluid comprises blowing dry air about the sealed measurement site to which the probe tip is applied.

22. The method of claim 21 which includes passing dry air coaxially about the probe tip and discharging the dry air peripherally about the probe tip on application to the measurement site, while employing the shield material to seal the measurement site by the application of gentle pressure of the shield material secured to and about the probe tip against the tooth surface.

* * * * *

UNITED STATES PATENT AND TRADEMARK OFFICE
CERTIFICATE OF CORRECTION

PATENT NO. : 4,215,698
DATED : August 5, 1980
INVENTOR(S) : Elie S. Nuwayser

It is certified that error appears in the above-identified patent and that said Letters Patent are hereby corrected as shown below:

In column 10, claim 13, line 13, delete "claim 1" and insert therefor --claim 12--.

Signed and Sealed this

Fourteenth Day of October 1980

[SEAL]

Attest:

SIDNEY A. DIAMOND

Attesting Officer

Commissioner of Patents and Trademarks